United States Patent
Lacko et al.

(10) Patent No.: US 12,208,146 B2
(45) Date of Patent: Jan. 28, 2025

(54) RECONSTITUTED HDL NANOPARTICLES FOR DELIVERY OF RADIOACTIVE AGENTS AND USES THEREOF

(71) Applicants: UNIVERSITY OF NORTH TEXAS HEALTH SCIENCE CENTER, Fort Worth, TX (US); THE AUTONOMOUS UNIVERSITY OF THE STATE OF MEXICO, Toluca (MX)

(72) Inventors: Andras G. Lacko, Fort Worth, TX (US); Laszlo Prokai, Mansfield, TX (US); Keila Isaac-Olivé, Toluca (MX)

(73) Assignees: UNIVERSITY OF NORTH TEXAS HEALTH SCIENCE CENTER, Fort Worth, TX (US); THE AUTONOMOUS UNIVERSITY OF THE STATE OF MEXICO, Toluca (MX)

( * ) Notice: Subject to any disclaimer, the term of this patent is extended or adjusted under 35 U.S.C. 154(b) by 858 days.

(21) Appl. No.: 17/294,701

(22) PCT Filed: Nov. 18, 2019

(86) PCT No.: PCT/US2019/061946
§ 371 (c)(1),
(2) Date: May 18, 2021

(87) PCT Pub. No.: WO2020/106605
PCT Pub. Date: May 28, 2020

(65) Prior Publication Data
US 2022/0008571 A1     Jan. 13, 2022

Related U.S. Application Data

(60) Provisional application No. 62/769,326, filed on Nov. 19, 2018.

(51) Int. Cl.
*A61K 51/12* (2006.01)
*A61K 51/04* (2006.01)
*A61P 35/00* (2006.01)
*C07D 213/807* (2006.01)

(52) U.S. Cl.
CPC ...... *A61K 51/1224* (2013.01); *A61K 51/0478* (2013.01); *A61P 35/00* (2018.01); *C07D 213/807* (2013.01)

(58) Field of Classification Search
CPC .. A61K 51/0478; A61P 35/00; C07D 213/807
See application file for complete search history.

(56) References Cited

U.S. PATENT DOCUMENTS

| | | |
|---|---|---|
| 2013/0058865 A1 | 3/2013 | Zhao |
| 2013/0171067 A1 | 7/2013 | Guminski et al. |

OTHER PUBLICATIONS

Laverman, P. et al. "A Novel Method to Label Liposomes with $^{99m}$Tc by the Hydrazino Nicotinyl Derivative" *The Journal of Nuclear Medicine*, Jan. 1999, pp. 192-197, vol. 40, No. 1.
Isaac-Olivé, K. et al. "[$^{99m}$Tc-HYNIC-N-dodecylamide]: a new hydrophobic tracer for labelling reconstituted high-density lipoproteins (rHDL) for radioimaging" Nanoscale, 2019, pp. 541-551, vol. 11.
Written Opinion in International Application No. PCT/US2019/061946, Feb. 3, 2020, pp. 1-4.

*Primary Examiner* — Robert S Cabral
(74) *Attorney, Agent, or Firm* — SALIWANCHIK, LLOYD & EISENSCHENK

(57) ABSTRACT

Despite the widespread use of nanotechnology in radio-imaging applications, lipoprotein based delivery systems received only limited attention so far. The subject application provides for the synthesis of a novel hydrophobic radio-imaging tracer. This tracer, comprising a hydrazinonicotinic acid (HYNIC)-N-dodecylamide and $^{99}$mTc conjugate can be encapsulated into rHDL nanoparticles (NPs). These rHDL NPs can selectively target the Scavenger Receptor type B1 (SR-B1) that is overexpressed on most cancer cells due to excess demand for cholesterol for membrane biogenesis and thus can target tumors in-vivo. Details of the tracer synthesis, characterization of rHDL/tracer complex, in-vitro uptake, stability studies and in-vivo application of this new radio-imaging approach are provided.

23 Claims, 7 Drawing Sheets

| Radioactive Nuclides of Rhenium | | | | |
|---|---|---|---|---|
| Radionuclide | Half-life | Mode of Decay | Energy of Radiations, Mev | Produced By |
| $Re^{178}$ | 15 m | $\beta^+$ | $\beta^+$: 3.1 | |
| $Re^{180}$ | 2.4 m | $\beta^+$, EC | $\beta^+$: 1.1<br>$\gamma$: 0.11, 0.88 | |
| $Re^{180}$ | 18 m | EC | $\gamma$: 0.227, 0.282 | |
| $Re^{180}$ | 20 h | $\beta^+$ | $\beta^+$: 1.9 | |
| $Re^{181}$ | 20 h | EC | $\gamma$: Many | |
| $Re^{182}$ | 12.7 h | EC | $\gamma$: Many | Daughter of $Os^{182}$ (21.9 h) |
| $Re^{183}$ | 71 d | EC | $\gamma$: Many | Daughter of $Os^{183}$ (13.5 h) |
| $Re^{184}$ | 50 d | EC | $\gamma$: Many | |
| $Re^{184}$ | 2.2 d | EC or IT | $\gamma$: 0.043, 0.159 | |
| $Re^{186}$ | 88.9 h | $\beta^-$, $\gamma$ | $\beta^-$: 0.934, 1.072<br>$\gamma$: 0.1372, 0.627, 0.764 | $Re^{185}(n,\gamma)Re^{186}$<br>$Os^{186}(n,p)Re^{186}$ |
| $Re^{188m}$ | 18.7 m | IT | $\gamma$: 0.0635, 0.105 | $Re^{187}(n,\gamma)Re^{188m}$ |
| $Re^{188}$ | 16.7 h | $\beta^-$, $\gamma$ | $\beta^-$: 1.96, 2.12<br>$\gamma$: 0.1551 | $Re^{187}(n,\gamma)Re^{188a}$ |
| $Re^{189}$ | 150 d | $\beta^-$, $\gamma$ | $\beta^-$: 0.2<br>$\gamma$: 1.0 | |
| $Re^{190}$ | 2.8 m | $\beta^-$, $\gamma$ | $\beta^-$: 1.7<br>$\gamma$: 0.191, 0.392, 0.57, 0.83 | |

Figure 9

RECONSTITUTED HDL NANOPARTICLES FOR DELIVERY OF RADIOACTIVE AGENTS AND USES THEREOF

CROSS-REFERENCE TO RELATED APPLICATIONS

This application is the U.S. National Stage Application of International Patent Application No. PCT/US2019/061946, filed on Nov. 18, 2019, which claims the benefit of U.S. Provisional Application Ser. No. 62/769,326, filed Nov. 19, 2018, the disclosures of which are hereby incorporated by reference in their entirety, including all figures, tables and amino acid or nucleic acid sequences.

FIELD OF THE INVENTION

The present invention relates generally to the fields of drug delivery, molecular biology and therapeutics. More particularly, it concerns high density lipoprotein (HDL) particles or reconstituted HDL (rHDL) particles for the delivery of radioisotopes to cancer cells.

BRIEF SUMMARY OF THE INVENTION

The subject application provides for the synthesis of a hydrophobic derivative of hydrazino-nicotinic acid (HYNIC) in order to prepare a conjugate, based on HYNIC/EDDA/tricine structure that can be encapsulated with high efficiency into the lipid core of HDL and be transported and internalized by (PC-3) prostate cancer (PC-3) cells (or other cancer cells) with the aim of visualizing a cancerous mass within a subject. The disclosed invention provides an avenue for improving the area of theranostics; combined imaging and therapy[37-39].

BRIEF DESCRIPTION OF THE DRAWINGS

FIG. 9. Radioactive Nuclides of Rhenium.

DETAILED DISCLOSURE OF THE INVENTION

Definitions

Figure 1B:
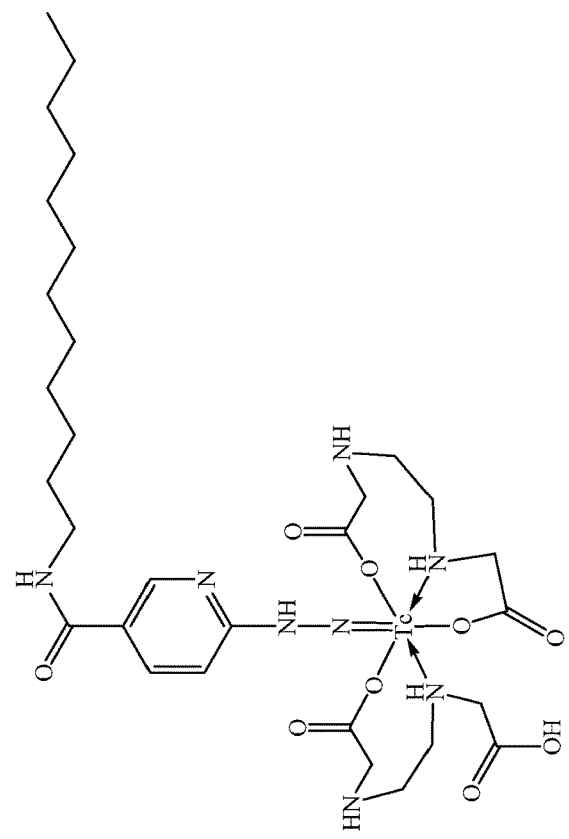
FIGS. 1A-1B. (A) Scheme for the synthesis of 6-hydrazinopyridine-3-carboxylic acid dodecylamide (HYNIC-DA). (B) Coordination chemistry of $^{99m}$Tc with HYNIC-DA and EDDA [46].

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value that varies from the numerical value set forth in this disclosure by ±10% or less. Thus, for any given numerical value, the variation may be ±1, ±2, ±3, ±4, ±5, ±6, ±7, ±8, ±9, or ±10%.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Further, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", include the phrases "consisting essentially of", "consists essentially of", "consisting", and "consists". The phrases "consisting essentially of" or "consists essentially of" indicate that the claim encompasses embodiments containing the specified materials or steps and those that do not materially affect the basic and novel characteristic(s) of the claim.

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0 etc.

A "subject" refers to either a human or non-human, such as primates, mammals, and vertebrates. In particular embodiments, the subject is a human.

"Treatment" and "treating" refer to administration or application of a therapeutic agent to a subject or performance of a procedure or modality on a subject for the purpose of obtaining a therapeutic benefit of a disease or health-related condition. For example, a treatment may include minimizing the growth or invasion of a tumor. The terms "treatment", "treat", "treating", and grammatical variants thereof, refer to the palliation or reduction in the frequency or severity of the signs or symptoms of a disease, such as a cancer. The term "therapeutic benefit" or "therapeutically effective" as used throughout this application refers to anything that promotes or enhances the well-being of the subject with respect to the medical treatment of a condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or reducing metastasis. Treatment of cancer may also refer to prolonging survival of a subject with cancer.

The phrases "pharmaceutical or pharmacologically acceptable" refers to molecular entities and compositions that do not produce an adverse, allergic or other untoward reaction when administered to an animal, such as a human, as appropriate. For animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. A pharmaceutically acceptable carrier is preferably formulated for administration to a human, although in certain embodiments it may be desirable to use a pharmaceutically acceptable carrier that is formulated for administration to a non-human animal but which would not be acceptable (e.g., due to governmental regulations) for administration to a human. Except insofar as any conventional carrier is incompatible with the active ingredient, its use in the therapeutic or pharmaceutical compositions is contemplated.

Also disclosed are methods of treating or imaging a subject with a cancer that involves administering to the subject a pharmaceutically effective amount of any of the aforementioned compositions that include a radiolabeled rHDL nanoparticle as disclosed herein. The subject can be any subject, such as a mouse, a rat, a rabbit, a cat, a dog, a cow, a horse, a sheep, a goat, a primate, or a human. In specific embodiments, the subject is a human, such as a human in need of a treatment or imaging.

Imaging can be performed by single photon emission computed tomography (SPECT) and/or X-ray computed tomography (CT) images of the subject to whom the radiolabeled rHDL NP is administered.

The pharmaceutical compositions can be administered using any method known to those of ordinary skill in the art. For example, the composition may be administered to the subject intravenously, topically, locally, systemically, intraperitoneally, intratracheally, intratumorally, intra-arterially, intramuscularly, endoscopically, intralesionally, percutaneously, subcutaneously, regionally, or by direct injection or perfusion. In specific embodiments, the composition is administered intravenously.

The cancer can be any type of cancer. For example, the cancer may be breast cancer, lung cancer, prostate cancer, ovarian cancer, brain cancer, liver cancer, cervical cancer, pancreatic cancer, colon cancer, colorectal cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, or leukemia.

Alternatively, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

Thus, the subject application provides the following non-limiting embodiments:

1. Reconstituted high-density lipoprotein (rHDL) nanoparticles (rHDL NPs) comprising hydrazinonicotinic acid (HYNIC)-N-dodecylamide.

2. The rHDL NPs of embodiment 1, wherein said hydrazinonicotinic acid (HYNIC)-N-dodecylamide is labeled with a rhenium (Re) or technetium (Tc) radioisotope, such as $^{92}$Tc, $^{93c}$Tc, $^{93g}$Tc, $^{93m}$Tc, $^{94g}$Tc, $^{94m}$Tc, $^{95g}$Tc, $^{95m}$Tc, $^{96g}$Tc, $^{96m}$Tc, $^{97m}$Tc, $^{99m}$Tc, $^{178}$Re, $^{180}$Re, $^{180}$Re, $^{180}$Re, $^{181}$Re, $^{182}$Re, $^{183}$Re, $^{184}$Re, $^{184}$Re, $^{186}$Re, $^{188m}$Re, $^{188}$Re, $^{189}$Re or $^{190}$Re (as identified in FIG. 9). Preferably, the Re and Tc radioisotopes emit gamma radiation for imaging purposes and emit beta raditaion for radiotherapy purposes.

3. A composition comprising a pharmaceutically acceptable carrier and an rHDL nanoparticle according to embodiments 1-2.

4. A method of treating or imaging cancer in a subject comprising administering a rHDL nanoparticle according to embodiment 2 or a composition according to embodiment 3 to a subject having a cancer.

5. The method according to embodiment 4, wherein said cancer expresses scavenger receptor type B1 (SR-B1).

6. The method according to embodiment 4 or 5, wherein said cancer is selected from breast cancer, colon cancer, ovarian cancer, prostate cancer, liver cancer, epithelial cancer, melanoma and lymphoma.

7. A method of synthesizing hydrazinonicotinic acid (HYNIC)-N-dodecylamide comprising reacting 6-chloropyridine-3-carboxylic acid with dodecylamine to form an amide and reacting said amide with hydrazine to form 6-hydrazinopyridine-3-carboxylic acid dodecylamide (HYNIC-DA).

8. The method according to embodiment 7, said method comprising contacting dodecylamine, 6-chloropyridine-3-carboxylic acid, 1-hydroxybenzotriazole and N,N'-diisopropylcarbodiimide.

9. The method according to embodiment 8, wherein said 1-hydroxybenzotriazole is anhydrous.

10. The method according to any one of embodiments 7-9, said method further comprising isolation of 6-chloropyridine-3-carboxylic acid dodecylamide.

11. The method according to embodiments 7-10, said method further comprising contacting said 6-chloropyridine-3-carboxylic acid dodecylamide with hydrazine to form hydrazinonicotinic acid (HYNIC)-N-dodecylamide.

12. The method according to embodiment 11, said method further comprising isolation of hydrazinonicotinic acid (HYNIC)-N-dodecylamide.

13. The method according to embodiments 7-12, said method further comprising contacting ethylenediamine-N, N'-diacetic acid (EDDA)-tricine solution SnCl$_2$ and $^{99m}$Tc-pertechnetate with HYNIC-DA to form $^{99m}$Tc radiolabeled HYNIC-DA.

14. The method according to embodiments 7-13, said method further comprising contacting said HYNIC-DA with rHDL to form rHDL comprising said HYNIC-DA, said HYNIC-DA being radiolabeled or not radiolabeled.

15. The method according to embodiment 14, wherein HYNIC-DA is not radiolabeled.

16. The method according to embodiment 14, wherein HYNIC-DA is radiolabeled.

17. The method according to embodiment 16, wherein HYNIC-DA is radiolabeled with a Tc or Re radioisotope, such as $^{92}$Tc, $^{93c}$Tc, $^{93g}$Tc, $^{93m}$Tc, $^{94m}$Tc, $^{95g}$Tc, $^{95m}$Tc, $^{96g}$Tc, $^{96m}$Tc, $^{97m}$Tc, $^{99m}$Tc, $^{178}$Re, $^{180}$Re, $^{180}$Re, $^{180}$Re, $^{181}$Re, $^{182}$Re, $^{183}$Re, $^{184}$Re, $^{184}$Re, $^{186}$Re, $^{188m}$Re, $^{188}$Re, $^{189}$Re or $^{190}$Re.

18. The method according to any one of embodiments 4-6, wherein said method comprises imaging a subject to whom radiolabeled rHDL are administered, said imaging being performed by Single photon emission computed tomography (SPECT) and/or X-ray computed tomography (CT) and said radiolabeled rHDL being labeled with a Tc or Re radioisotope that emits gamma radiation.

19. The method according to any one of embodiments 4-6, wherein said method comprises treating a subject having cancer subject to whom radiolabeled rHDL are administered, said radiolabeled rHDL being labeled with a Tc or Re radioisotope that emits beta radiation.

EXAMPLES

Materials and Methods

Chemicals, Supplies, and Instruments

Chemicals (Egg yolk phosphatidylcholine, free cholesterol and cholesterol ester) need for rHDL synthesis were ordered from Sigma Aldrich. Apolipoprotein A1 was ordered from MC Labs, South San Francisco, CA. Dodecylamine and anhydrous 1-hydroxybenzotriazole were obtained from ACROS Organics (Geel, Belgium) and AnaSpec (Fremont, CA.), respectively. All other chemicals were obtained from Sigma-Aldrich (St. Louis, MO, USA). Reactions were performed using a Wheaton (Millville, NJ, USA) Micro Kit, and isolation of the reaction products was performed using commercial labware. Melting points (m.p.) were determined using an electrothermal apparatus (Mel-Temp®, Barnstead International, Dubuque, Iowa, USA) and reported without correction. Mass spectra were recorded on a linear ion trap (LTQ) and a linear ion trap-Orbitrap (LTQ Velos Orbitrap Pro) hybrid instrument (both from Thermo Fisher Scientific, San Jose, CA, USA) using an atmospheric pressure solids analysis probe (ASAP; M&M Mass Spec Consulting, Newark, DE, USA) as described in the literature[40]. For accurate-mass measurements by the Orbitrap, nominal resolution (M/ΔM, at m/z 400) were set to 50000 and internal calibration was done after acquisition using RecalOffline (version 2.2.0115) and protonated dioctyl phthalate (m z 391.2843) as reference ion[41]. H-Nuclear magnetic resonance (NMR) spectra were obtained at 300 MHz on a Bruker (Billerica, MA, USA) Fourier 300 HD instrument in dimethyl-d$_6$ sulfoxide (DMSO-d$_6$) containing tetramethylsilane as an internal reference.

Synthesis of HYNIC-N-codecylamide

Figure 1A:
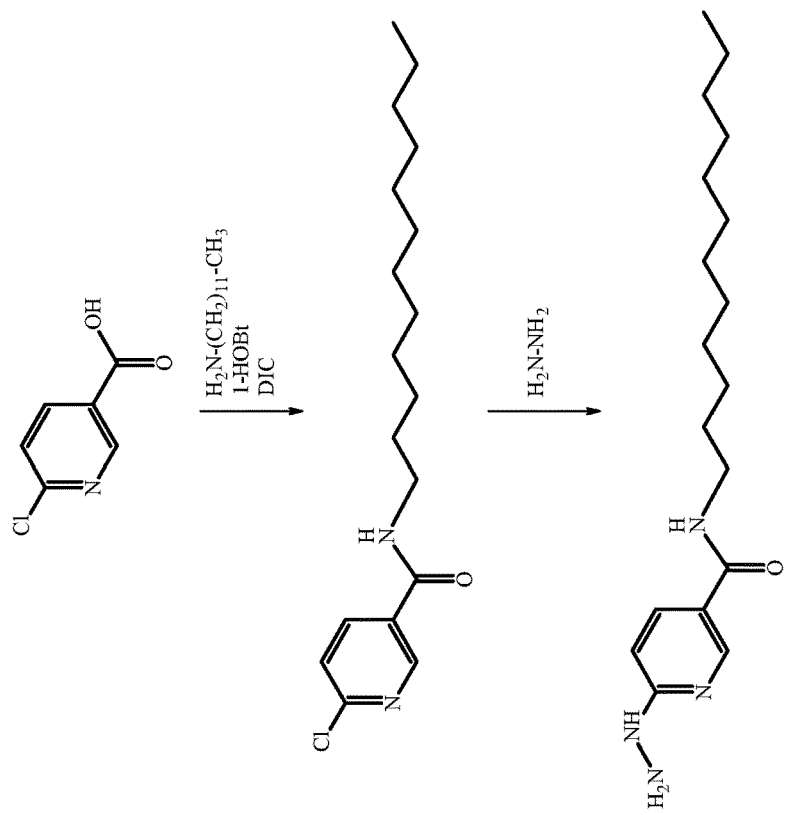

The synthesis was carried out in two steps, starting from 6-chloropyridine-3-carboxylic acid. The first step was the reaction with dodecylamine to form the amide as shown in FIGS. 1A-1B. The second reaction involved the substitution of the 6-Cl by hydrazine to form 6-hydrazinopyridine-3-carboxylic acid dodecylamide (HYNIC-DA). FIG. 1B also shows the coordination chemistry for $^{99m}$Tc-radioisotope.

6-Chloropyridine-3-carboxylic Acid Dodecylamide

Dodecylamine (0.93 g, 5 mmol), 6-chloropyridine-3-carboxylic acid (0.79 g, 5 mmol) and anhydrous 1-hydroxybenzotriazole (1-HOBt; 0.75 g, 5.6 mmol) were dissolved in 3 mL dichloromethane. After the addition of N,N'-diisopropylcarbodiimide (DIC; 860 µl~0.70 g, 5.6 mmol), the reaction vial was capped and the mixture was stirred overnight on room temperature using a Teflon®-coated cylindrical magnetic bar and a laboratory stirrer/hot plate (Corning, Acton, MA, USA). Completion of the reaction was confirmed by ASAP mass spectrometry. The crude product was isolated by vacuum filtration, and was recrystallized from dichloromethane. Off-white solid, 1.25 g (~75% yield); m.p. 100° C.; ASAP-MS: m/z 325 and 327 (for $^{35}Cl$ and $^{37}Cl$ isotopes, respectively, ~3:1 ratio of ion abundance); HR-MS: m/z 325.2037, $\Delta=-1.3$ ppm for $C_{18}H_{30}N_2O^{35}Cl$ (MH$^+$) and 327.2010, $\Delta=-0.5$ ppm for $C_{18}H_{30}N_2O^{37}Cl$ (MH$^+$); $^1$H-NMR ($\delta$, ppm): 8.81 (s, J=0.6 Hz, 1H, pyridinium H-2), 8.22 (d, J=8.4 and 0.9 Hz, 1H, pyridinium H-4), 7.64 (d, J=8.4 Hz, 1H, pyridinium H-5), 3.26 (dt, J=7.8 and 6.8 Hz, 2H, $\alpha$-CH$_2$ of dodecylamide), 1.51 (m, 2H, $\beta$-CH$_2$ of dodecylamide), 1.20-1.32 (bs, 18H, $\gamma$-CH$_2$ to $\lambda$-CH$_2$ of dodecylamide), 0.87 (t, J=6.2 Hz, 3H, CH$_3$ of dodecylamide).

6-Hydrazinopyridine-3-carboxylic Acid Dodecylamide (Hydrazinonicotinoic Acid Docecylamide, HYNIC-DA)

To the isolated 6-chloropyridine-3-carboxylic acid dodecylamide (1 g, ~3 mmol), two mL of reagent alcohol was added in a 10-mL reaction vial fitted with a water-cooled jacketed condenser. The mixture was brought into reflux under stirring using the stirrer/hot plate (from Corning, see the previous paragraph) and a Teflon®-coated cylindrical magnetic bar. Then, 0.5 mL of hydrazine/water solution (85/15, v/v) was added drop-wise through the condenser using a disposable glass pipette, and the reaction was allowed to proceed under reflux for 2 hours. Completion of the reaction was confirmed by ASAP mass spectrometry. After cooling, the suspension was poured into 5 mL of ice-cold water, and the product was isolated by vacuum filtration followed by washing with water and, then, 1% HCl solution (w/v) 5 mL each, followed by drying the isolated product in a vacuum desiccator. Grey-white solid, 0.52 g (~50% yield); m.p. 208° C.; ASAP-MS: m/z 321; HR-MS: m/z 321.2639, $\Delta=-3.0$ ppm for $C_{18}H_{33}N_4O$ (MH$^+$); $^1$H-NMR ($\delta$, ppm): 8.60 (d, J=2.0 Hz, 1H, pyridinium H-2), 8.12 (dd, J=8.8 and 2.0 Hz, 1H, pyridinium H-4), 6.91 (d, J=8.8 Hz, 1H, pyridinium H-5), 3.23 (dt, J=8.0 and 6.8 Hz, 2H, $\alpha$-CH$_2$ of dodecylamide), 1.50 (p, J=8.0 Hz, 2H, $\beta$-CH$_2$ of dodecylamide), 1.24-1.28 (bs, 18H, $\gamma$-CH$_2$ to $\lambda$-CH$_2$ of dodecylamide), 0.85 (t, J=7.0 Hz, 3H, CH$_3$ of dodecylamide).

Liposome and rHDL Preparation and Characterization

Liposome Preparation

Chemicals were purchased from Avanti Polar Lipids, Inc. (Alabaster, AL, USA). Liposomes were prepared according to the method reported by Toro-Córdova et al.[42] which is a variation of the reverse-phase evaporation method reported in the literature[43]. Briefly, the lipid combination soybean 1-α-phosphatidylcholine (HSPC); 1,2-distearoyl-sn-glycero-3-phosphoethanolamine-N-[methoxy (polyethylene glycol)-2000] (DSPE-mPEG2000); and cholesterol in a ratio HSPC: DSPE-mPEG2000:cholesterol (60%:5%:35%) was dissolved in chloroform:methanol (2:1) and added dropwise to double distilled water (DDW) at 70° C. The resulting mixture was subjected to fast agitation to produce a water-in-oil emulsion. Solvents were evaporated in a round flask under sonication with the resulting formation of liposomes. Particle size was reduced by sonication and homogenization by passing once through various membrane filters (once through 400 nm membrane, a twice through a 200 nm membrane and four times through a 100 nm membrane). Liposomes were finally suspended in a known DDW volume.

Liposome Characterization

The physicochemical characterization of liposomes included the phospholipid quantification, determination of particle size and zeta potential. Phospholipid determination in the final liposome suspension was done by the Stewart method[44]. Particle size and zeta potential measurements (5 repetitions) of the colloidal solution were carried out using a particle size (dynamic light scattering) and Z potential analyzer (Nanotrac Wave, Model MN401, Microtract, FL, USA).

rHDL Preparation rHDL synthesis was accomplished by a procedure developed earlier[18] (the disclosure of which is hereby incorporated by reference in its entirety). Briefly, a mixture of egg yolk phosphatidylcholine (EYPC), free cholesterol (FC), and cholesteryl oleate (CE), was prepared in chloroform. The lipid mixture (EYPC, FC, and CE) were dried under nitrogen to a thin film and dispersed in 60 µL DMSO. To this mixture, Apo A-I (5 mg) and 140 µl sodium cholate (from a stock of 100 mM) were added and the volume was made up to 2 ml with Tris-ethylenediaminetetraacetic acid (EDTA) buffer (10 mM Tris, 0.1 M KCl, 1 mM EDTA pH 8.0). The final EYPC to cholate molar ratio was maintained at (1:1.6). The lipid/protein/cholate mixture was then incubated for 12 h at 4° C., followed by dialysis against 2 L of phosphate buffer saline (PBS) for 48 h with three buffer changes in the first 12 h. The preparations were then centrifuged at 1000 rpm for 2 min and filtered using a 0.2 µm syringe filter. The preparations were kept in the dark at 4° C. until further use.

rHDL Characterization

Phospholipid content was determined by an enzymatic reagent kit (phospholipid C) using microtiter plate assays as per manufacturer's suggestions. Protein determinations were carried out using a BCA protein assay kit. Particle size and zeta potential measurements (5 repetitions) of the colloidal suspension were carried out using a particle size (dynamic light scattering) and Z potential analyzer (Nanotrac Wave, Model MN401, Microtract, FL, USA).

Preparation and Characterization of $^{99m}$Tc-BMEDA and $^{99m}$Tc-HYNIC-DA $^{99m}$Tc-BMEDA Radiolabelling was carried out according to the method used by Santos Cuevas et al.[45]. One hundred mg of N,N-bis(2-mercaptoethyl)-N',N'-diethyl-ethylenediamine BMEDA (ABX-Germany) were dissolved in 1 mL of saline solution (0.9% NaCl). Five µL of 10 fold diluted solution (50 µg, 0.224 µmol, 223.27 g/mol) was added to 25 µL of $^{99m}$Tc-pertechnetate (GETEC-ININ-Mexico, Ocoyoacac Mex, Mexico; 740-925 MBq) followed by 7 µL of deprotection mixture (50 mg/mL sodium tartrate in 0.1 M NH$_4$OH/NH$_4$CH$_3$COOH, pH 5) and 5 µL of reducing solution (1 mg/ml SnCl$_2$, in 0.012 mol/L HCl). The final mixture was incubated for 20 min at room temperature. This complex was used to compare the retention times during HPLC measurements.

$^{99m}$Tc-HYNIC-DA

Radiolabelling was carried out by adding 500 µL of EDDA-tricine solution (30 mg of EDDA in 1.5 mL of 0.1 mol/L NaOH and 60 mg of tricine in 1.5 mL of 0.2 mol/L phosphate buffer, pH=7), 25 µL of SnCl$_2$ solution (1 mg/ml, in 0.012 mol/1 HCl), 500 µL of saline solution, and 25 µL of $^{99m}$Tc-pertechnetate (GETEC-ININ-Mexico, Ocoyoacac Mex, Mexico; 740-925 MBq) to 200 µL HYNIC-DA (1 mg/ml in ethanol, 0.621 µmol, 321.70 g/mol), followed by incubation at 92° C. for 20 min in a dry block heater.

Radiochemical Purity

The radiochemical purity in both cases ($^{99m}$Tc-BMEDA and $^{99m}$Tc-HYNIC-DA) was determined by instant thin-layer chromatography on silica gel (ITLC-SG) using saline solution as a solvent, and reversed phase HPLC on a C18 column (µBondapak C18 column; Waters) using a Waters Empower system with an inline radioactivity detector and a gradient of water/acetonitrile containing 0.1% TFA from 95/5 (v/v) to 20/80 (v/v) over 35 min at a flow rate of 1 ml/min. Using this system, free $^{99m}$TcO$_4^-$ is dissolved in the solvent and moves (ITLC-SG) out in HPLC exhibiting a $t_R$=3-3.5 min.

Hydrophobicity and Partition Coefficient (Log P) for $^{99m}$Tc-BMEDA and $^{99m}$Tc-HYNIC-DA: Experimental Determination 20 µL of each $^{99m}$Tc complex was added into a mixture of equal volumes of 1-octanol and water (500 uL) and incubated overnight on a shaker. After the layer separation, 20 µL of each layer was taken and counted in a well-gamma counter. The partition coefficient was calculated as the logarithm of the quotient (counts in the 1-octanol phase)/(counts in the aqueous phase).

Liposome and HDL Labeling Efficiencies

10 µL of $^{99m}$Tc-BMEDA solution (11.9 µg, 0.05 µmol) and 100 µL of $^{99m}$Tc-HYNIC-DA solution (16 µg, 0.05 µmol) were added to liposomes (1 mL) respectively and incubated at 40° C. for 60 minutes. Exactly, the same procedure was employed for labeling HDL nanoparticles. The $^{99m}$Tc-compounds were separated from free $^{99m}$Tc-BMEDA/$^{99m}$Tc-HYNIC-DA using a PD-10 column eluted with normal saline solution. Each 0.5 mL fraction was collected into a tube and counted using a gamma counter. The opacity of liposomes and HDL was used to visually monitor the collection of the $^{99m}$Tc-liposomes and $^{99m}$Tc-rHDL respectively. The labeling efficiency was determined from the radio-chromatogram as the ratio of the counts from the liposome/HDL fractions divided by the total counts from all collected fractions.

In all cases ($^{99m}$Tc-BMEDA-Liposomes, $^{99m}$Tc-HYNIC-DA-Liposomes, $^{99m}$Tc-BMEDA-HDL and $^{99m}$Tc-HYNIC-DA-rHDL), the fifth fraction of the radio-chromatogram was centrifuged in a dialysis tube MWCO of 100,000 Da at 2500 g for 15 min. The fraction representing MW less than 100,000 Da was counted using a gamma counter, and the fraction with MW higher than 100,000 Da was taken out from the tube.

In Vitro Stability of Labeled Liposomes and Labeled HDL in Human Serum

To determine the stability of $^{99m}$Tc-BMEDA-Liposomes, $^{99m}$Tc-HYNIC-DA-Liposomes, $^{99m}$Tc-BMEDA-rHDL, $^{99m}$Tc-HYNIC-DA-rHDL in serum, 150 µL of the fifth fraction eluted from the PD-10 column (most opaque fraction containing the labeled liposomes/HDL: concentration 0.33 mg/mL)) was incubated at 37° C. with 5 mL of 5× diluted human serum. The radiochemical stability of the labeled liposomes/HDL was determined by taking 1 mL of the incubated particles at different time points following the addition of 300 µL of TFA for protein precipitation. Samples were centrifuged at 2000 rpm for 3 min, and the whole sample, the pellet and supernatant radioactivities were determined in a gamma counter. Pellet activity represents the activity of the labeled liposomes/HDL since liposomes and HDL are associated with the precipitated protein. Any instability in the system, recognized as a leak of the $^{99m}$Tc-BMEDA or $^{99m}$Tc-HYNIC-DA compounds from the liposomes/HDL, would be determined in the supernatant. Control samples were analyzed to demonstrate that neither $^{99m}$Tc-BMEDA nor $^{99m}$Tc-HYNIC-DA precipitates by TFA. In this case, the procedure was the same as already described except adding 150 µL of $^{99m}$Tc-BMEDA or $^{99m}$Tc-HYNIC-DA compounds to serum albumin instead of the labeled liposomes/rHDL.

Cell Uptake Experiments

PC3 cells were harvested and diluted in fresh medium ($1\times10^5$ cells/well, 0.5 mL) and then seeded in 24-well tissue culture plates. After 24 h, the medium was removed, and the cells were incubated with 100 µL/well of phosphate buffered saline (PBS) and the following treatments per well: 2 kBq of $^{99m}$TcO4−, and 30 µL of 1 µg/µL of $^{99m}$Tc-rHDL, $^{99m}$Tc-Liposome, and $^{99m}$Tc-HYNIC-DA for 45 min at 37° C. Then, cells were rinsed two times with 0.5 mL of ice-cold PBS. These two washes were combined and represent the $^{99m}$TcO$_4^-$, $^{99m}$Tc-rHDL, $^{99m}$Tc-Liposome, and $^{99m}$Tc-HYNIC-DA not bounded to cells. Cells were washed with 1 mL of PBS and later were incubated twice with 0.5 mL of Glycine-HCl (50 mM, pH 2.8). The Glycine-HCl washes were combined, these washed recovered the $^{99m}$TcO$_4^-$, $^{99m}$Tc-rHDL, $^{99m}$Tc-Liposome, and $^{99m}$Tc-HYNIC-DA adhered or bounded to cell membrane. Cells were washed with 1 mL of PBS, and finally were washed twice with 0.5 mL of 1.0 M NaOH (lysed cells) to recover the $^{99m}$TcO$_4^-$, $^{99m}$Tc-rHDL, $^{99m}$Tc-Liposome, and $^{99m}$Tc-HYNIC-DA internalized in the cytoplasm (washes were combined). Radioactivity was measured in the initial PBS, Glycine-HCl and NaOH combined washes using a NaI(Tl) detector (NML Inc. USA). The initial activity of each treatment was taken to represent 100% of activity. In parallel, the nonspecific binding was determined using 30 µL of 60 µg/µL of unlabeled rHDL, which blocked SR-B1 receptors on PC3 cells.

$^{99m}$Tc-HYNIC-DA-HDL Biodistribution and Imaging Studies

In-vivo studies in mice were carried out according to the rules and regulations of the Official Mexican Norm 062-ZOO-1999. Normal male Balb/c mice and athymic nude mice, 6-7 weeks, were kept in sterile cages with sterile wood-shaving beds, constant temperature, humidity, noise, and 12 hr light/dark cycles. Water and feed (standard PMI 5001 feed) were given ad libitum.

Normal Mice

Normal male Balb/c mice were injected in the tail vein with $^{99m}$Tc-HYNIC-DA-rHDL (200 µl, 3 MBq) under 2% isoflurane anesthesia. The mice were sacrificed at 0.5, 2, 4 and 24 h (3 mice for each time point) after radiopharmaceutical administration. Whole heart, lungs, liver, spleen, kidneys, and samples of blood, intestines, bone, muscle, pancreas, and brain were transferred to pre-weighed plastic test tubes or bags. The activity was determined in a well-type scintillation detector along with two aliquots of a diluted standard representing 100% of the injected dose. The mean activities were used to obtain the percentage of injected activity per gram of tissue.

Mice Bearing PC3 Tumor

For tumor studies two tumor models in athymic mice (6-7 weeks) were studied. In the first one, mice were inoculated with PC3 cells subcutaneously in the upper back and in the second one; mice were inoculated with PC3 cells by injection into the tail vein. In both cases $2\times10^6$ PC3 cancer cells suspended in 0.1 ml PBS were used.

Subcutaneous inoculation: In the case of the subcutaneous tumor inoculation, the injection sites were observed at regular intervals for tumor formation and progression. Once the tumor was observed in the mice upper back, mice were injected in the tail-vein or intra-tumour with $^{99m}$Tc-rHDL (200 μL, 3 MBq) under 2% isoflurane anesthesia. In both cases, mice were sacrificed at 24 h (n=3 for each mice) after radiopharmaceutical administration, and in the case of intra-tumoral injection they were also sacrificed after 5 min post-injection. Whole heart, lungs, liver, spleen, kidneys, tumor, and samples of blood, intestines, bone, pancreas, and muscle were transferred to pre-weighed plastic test tubes. The activity was determined in a well-type scintillation detector along with two aliquots of a diluted standard representing 100% of the injected dose. The mean activities were used to obtain the percentage of injected activity per gram of tissue (% ID/g) and the percentage of injected activity per organ (% ID/organ). $^{99m}$Tc-SPECT/CT Imaging Single photon emission computed tomography (SPECT) and X-ray computed tomography (CT) images were acquired at 4 h after the injection of $^{99m}$Tc-rHDL using a micro SPECT/CT scanner (Albira, ONCOVISION; Gem Imaging S.A., Valencia, Spain) to verify the PC3 tumor uptake. Mice under 2% isoflurane anesthesia were placed in the prone position and half body (torax) imaging was performed. The micro-SPECT field of view was 40 mm, a symmetric 20% window was set at 140 keV and multi pinhole collimators were used to acquire a 3D SPECT image with a total of 64 projections of 30 s, over 360°. The image dataset was then reconstructed using the ordered subset expectation maximization (OSEM) algorithm with standard mode parameter as provided by manufacturer. CT parameters were 35 kV sure voltage, 700 μA current and 600 micro-CT projections.

Tail vein inoculation: After tail vein injection, it is expected that tumor growths in the pulmonary vasculature. Ten days after the tumor inoculation, mice were injected (200 μL, 3 MBq) in the tail-vein with $^{99m}$Tc-rHDL and $^{99m}$Tc-Liposomes respectively (n=3 each) under 2% isoflurane anesthesia. SPECT and radiographic computed tomography (CT) images were acquired at 0.5, 2, 4 and 24 h after radiopharmaceutical injection using a micro-SPECT/CT scanner (Albira, ONCOVISION; Gem Imaging S.A., Valencia, Spain) in the same conditions described above. From the radiopharmaceuticals $^{99m}$Tc-rHDL and $^{99m}$Tc-Liposomes injected doses, and the weight of each mouse, the mean standardized uptake value in the tumor (SUV mean) was calculated using PMOD Data Analysis Software (PMOD Technologies).

Radiokinetic $^{99m}$Tc-HYNIC-DA-HDL

From the percentages of injected dose per organ (% ID/Organ) at different times in the main target organs (determined from the biodistribution), the $A_h(t)$ functions were obtained ($A_h(t)$ $q_h(t)$ $e^{-(\lambda_B + \lambda_R)t}$) and the total number of disintegrations N (MBq.h/MBq) of $^{99m}$Tc in the organ normalized to unit-administered activity was also calculated. The $A_h(t)$ functions and total number of disintegrations N (MBq.h/MBq) in the tumor was also calculated for $^{99m}$Tc-rHDL and $^{99m}$Tc-Liposome administrations.

Results and Discussions

The combination of HYNIC and the ethylenediamine-N,N'-diacetic acid (EDDA) with tricine has been successfully employed as a bi-functional chelator for labeling peptides and gold nanoparticles with $^{99m}$Tc due to its the high stability with the HYNIC imine bond. The EDDA/tricine completes the coordination sphere of the $^{99m}$Tc complex[46-48]. This $^{99m}$Tc-HYNIC/EDDA/tricine complex is suitable for in vivo studies as it facilitates urinary excretion (hydrophilic properties) of the isotope. However, a hydrophilic compound would not be efficiently encapsulated into the core of the rHDL unless it is modified to have hydrophobic properties as described herein. Specifically, HYNIC-DA was synthesized as a lipophilic derivative of HYNIC (see Methods section) to facilitate incorporation of a bi-functional chelator-complexed $^{99m}$Tc into liposomes and rHDL nanoparticles. FIG. 1 shows the synthetic scheme for HYNIC-DA (FIG. 1A) as well as state-of-the-art of $^{99m}$Tc co-ordination chemistry (FIG. 1B).[49]

Liposome and HDL Characterization

Data on the characterization of liposomes and HDL are shown in Table 1. As can be seen, the liposomal NPs are much larger than the rHDL NPs, while both were found to be very stable (colloidal stability) in suspension, as indicated by their respective Z-potentials. Both nanoparticles had an acceptable homogeneity as indicated by the observed polydispersity index values.

TABLE 1

Characterization of the liposome and HDL nanoparticles

| Parameter | Liposomes | rHDL |
|---|---|---|
| Particle diameter (nm) | 107.4 ± 15 | 36.60 ± 10 |
| Polydispersity | 0.186 ± 0.04 | 0.28 ± 0.05 |
| Z-potential (mV) | −18.15 ± 6 | −20.60 ± 7 |
| Phospholipid (mg/mL) | 23.34 ± 4 | 1.55 ± 0.6 |
| Protein (mg/mL) | N/A | 1.19 ± 0.3 |

Preparation of $^{99m}$Tc-BMEDA and $^{99m}$Tc-HYNIC-DA

The method used in this work for the labeling of BMEDA with $^{99m}$Tc was different compared to the conventional glutathione encapsulated liposomes method[50]. In the conventional approach, the liposome is pre-loaded with reduced glutathione (GSH), and $^{99m}$Tc is complexed with BMEDA through $^{99m}$Tc-glucoheptonate in three steps: (i) uploading liposomes with GSH, (ii) preparing the $^{99m}$Tc-glucoheptonate from $^{99m}$TCO$_4^-$, and (iii) preparing the $^{99m}$Tc-BMEDA complex ($^{99m}$Tc-"SNS/S" type of complex). The labeling efficiency of this method is usually limited (below 85%). During these studies, the liposomes were not employed for BMEDA labeling with $^{99m}$Tc. Instead the $^{99m}$Tc-BMEDA was prepared in a single step using the same methodology reported earlier[51] to prepare a $^{99m}$Tc-N$_2$S$_2$ complex. This method facilitates a simpler and more efficient labeling procedure. The radiochemical purity of the product determined by ITLC-SG and HPLC was 90-95%.

The $^{99m}$Tc-labeling of HYNIC-DA was also carried out in one step, following the methodology already reported to form $^{99m}$Tc-HYNIC complex[45]. As with the $^{99m}$Tc-BMEDA, the radiochemical purity, determined by ITLC-SG and HPLC was within 90-95%.

Figure 2:
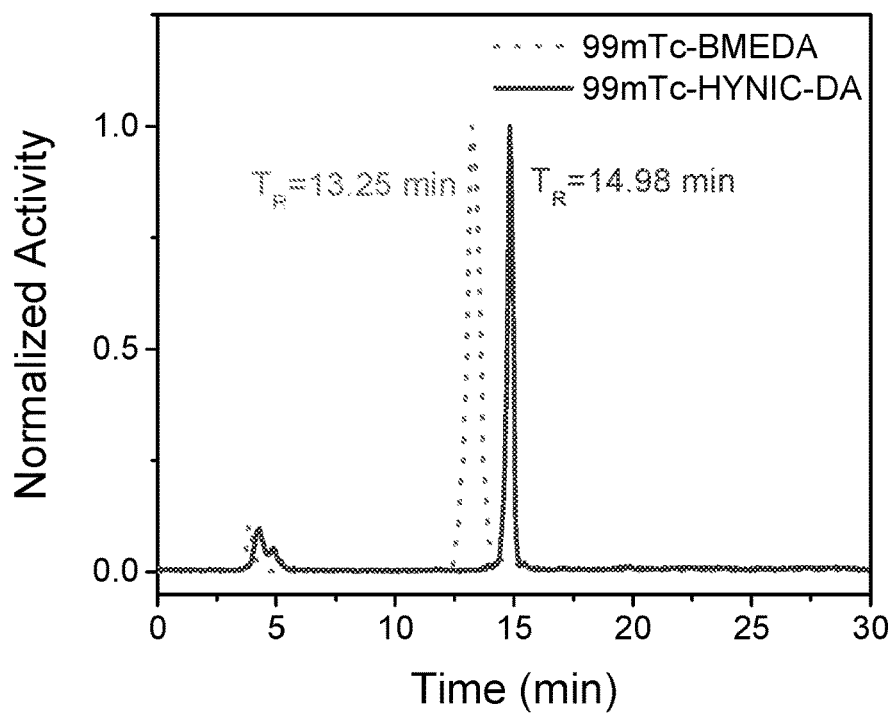
FIG. 2. RP-HPLC radio-chromatogram of $^{99m}$Tc-BMEDA and $^{99m}$Tc-HYNIC-DA complexes.

Hydrophobicity and Partition Coefficient (Log P) for $^{99m}$Tc-BMEDA and $^{99m}$Tc-DA-HYNIC The hydrophobicity is directly proportional to the retention time of RP-HPLC, as previously reported[52]. FIG. 2 shows The RP-HPLC radio-chromatogram of $^{99m}$Tc-HYNIC-DA and $^{99m}$Tc-BMEDA. These data show that $^{99m}$Tc-HYNIC had a higher retention time (1.73 min higher) than $^{99m}$Tc-BMEDA, indicating that it is more hydrophobic. These findings agree with the experimental partition coefficient determined for these compounds, −1.30 for $^{99m}$Tc-BMEDA and 0.25 for $^{99m}$Tc-HYNIC-DA (the real complex is $^{99m}$Tc-HYNIC-DA/EDDA, since HYNIC cannot complete the coordination sphere of $^{99m}$Tc and EDDA is therefore used for this purpose). The negative value for $^{99m}$Tc-BMEDA and the positive value for $^{99m}$Tc-HYNIC indicate that $^{99m}$Tc-HYNIC-DA is more hydrophobic than $^{99m}$Tc-BMEDA, and the difference in hydrophobicity is slightly over one log unit. When estimated by the method built into the Chem3D molecular modeling software, the log P for BMEDA was found to be 1.54, while for HYNIC-DA it was 3.85. The hydrophobicity of these molecules is reduced with the formation of the metal complexes, but the trend is maintained in that HYNIC-DA molecule, which is more hydrophobic than BMEDA; i.e. $^{99m}$Tc-HYNIC-DA remains more hydrophobic than $^{99m}$Tc-BMEDA as expected. From these findings, it is anticipated that $^{99m}$Tc-HYNIC-DA can be incorporated into the hydrophobic layer of liposomes and into the hydrophobic core of HDL more efficiently than $^{99m}$Tc-BMEDA.

Liposome and HDL Labeling Efficiencies

Figure 3:
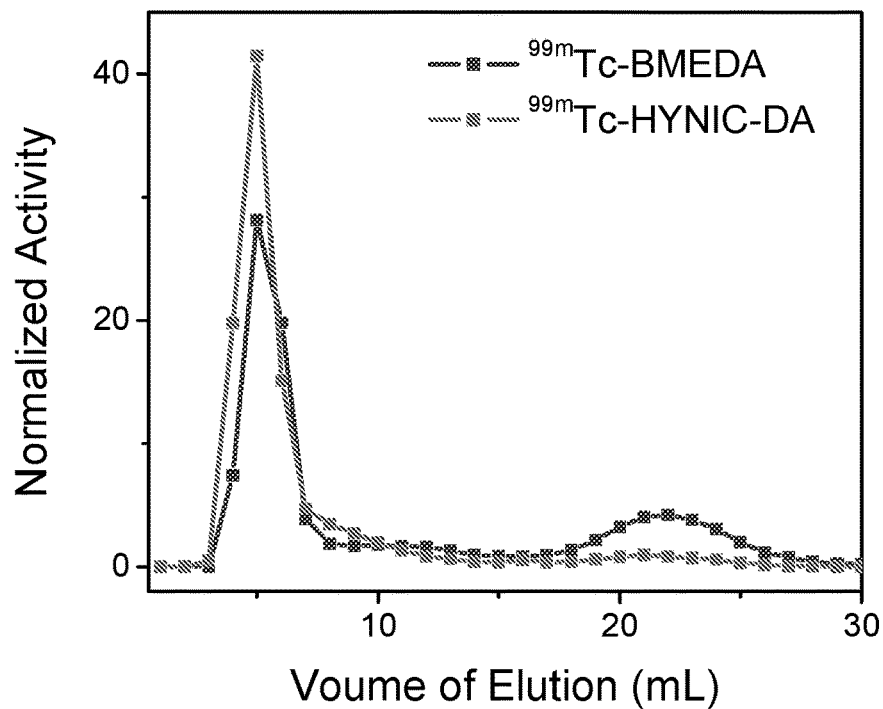
FIG. 3. Labelling efficiency of HDL fractions collected at different elution times.

FIG. 3 shows the labeling efficiency of liposomes and rHDL with $^{99m}$Tc-BMEDA and $^{99m}$Tc-HYNIC-DA respectively. For both nanoparticles, the labeling efficiency is always higher with $^{99m}$Tc-HYNIC-DA than $^{99m}$Tc-BMEDA.

100,000 Da. All the radioactivity was found inside the membrane, meaning that no aggregation of $^{99m}$Tc-complexes was present (any $^{99m}$Tc-complex aggregation would have a molecular weight of less than 100,000 Da). This confirms that the $^{99m}$Tc-complexes were associated with the rHDL NPs.

In Vitro Stability of Labeled Liposomes and Labeled HDL in Human Serum

Stability is understood as the capacity of $^{99m}$Tc-BMEDA and $^{99m}$Tc-HYNIC-DA for remaining entrapped into the HDL without leaking. Results presented in Table 2 are in agreement with those reported in earlier sections. The lower hydrophobicity of $^{99m}$Tc-BMEDA in comparison to $^{99m}$Tc-HYNIC-DA explains the higher stability and retention of $^{99m}$Tc-HYNIC-DA into the nanoparticles. After 3 h of incubation, more than 90% of $^{99m}$Tc-HYNIC-DA is still inside the liposomes and HDL. Due to lower stability of the BMEDA, it was not used in the animal studies.

TABLE 2

Results of the in vitro stability test for liposomes and rHDL nanoparticles in human serum.

| Time (h) | $^{99m}$Tc-BMEDA-Liposomes | $^{99m}$Tc-HYNIC-DA-Liposome | $^{99m}$Tc-BMEDA-rHDL | $^{99m}$Tc-HYNIC-DA-rHDL |
|---|---|---|---|---|
| 1 | 92 ± 5 | 98 ± 2 | 100 | 100 |
| 2 | 80 ± 3 | 95 ± 1 | 87 ± 5 | 100 |
| 3 | 73 ± 6 | 91 ± 3 | 78 ± 2 | 96.5 ± 0.6 |

For liposomes, yields were (66±2) % vs (61±2) % respectively while for rHDL yields were (86±3) % vs (57±3) %. For both $^{99m}$Tc-complexes, the labeling efficiency of rHDL was always higher than that of the liposomes. These differences are explained by the relative hydrophobicities of these $^{99m}$Tc-conjugates ($^{99m}$Tc-HYNIC-DA is more hydrophobic).

Figure 4:
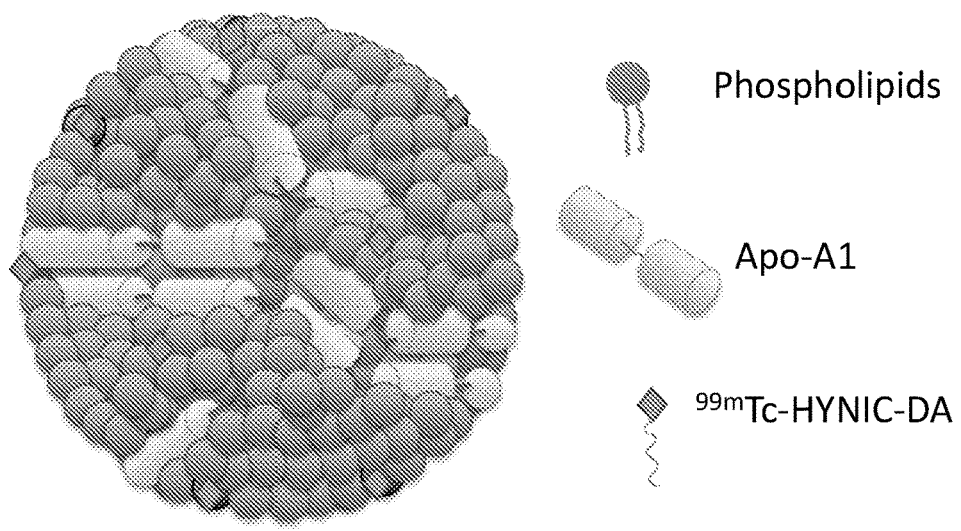
FIG. 4. Schematic structure of the labeled rHDL with the localization of HYNIC-DA.

Schematically, the labeled HDL with $^{99m}$Tc-HYNIC-DA can be represented as shown in FIG. 4. The blue spheres represent the phospholipids and cholesterol forming the outer region; the orange diamonds represent the $^{99m}$Tc-complex ($^{99m}$Tc-BMEDA or $^{99m}$Tc-HYNIC-DA) while the tail of the DA molecule is buried in the core of the particle. The green cylinders represent the amphipathic peptide chain of the Apo A-1 protein stabilizing the spherical structure of rHDL nanoparticles making it water soluble.

$^{99m}$Tc-BMEDA is the conventional labeling agent for liposomes, but usually, liposomes are loaded with glutathione (GSH) in the inner core, so once the $^{99m}$Tc-BMEDA passes through the hydrophobic outer shell it reaches the hydrophilic core and there $^{99m}$Tc-BMEDA is reduced by GSH becoming more hydrophilic and entrapped in the central core[50]. During these studies, the liposomes were not loaded with GSH; therefore both $^{99m}$Tc-BMEDA and $^{99m}$Tc-HYNIC-DA remained in the outer hydrophobic shell of liposomes. Finally, the lipid layer of HDL is hydrophobic; therefore, both $^{99m}$Tc-complexes are loaded inside the NP via HYNIC-DA conjugate (FIG. 4). Because $^{99m}$Tc-HYNIC-DA is more hydrophobic (larger log P and retention time in RP-HPLC), it has a larger distribution in hydrophobic areas than, $^{99m}$Tc-BMEDA, that facilitates higher labeling efficiency.

Figure 7:
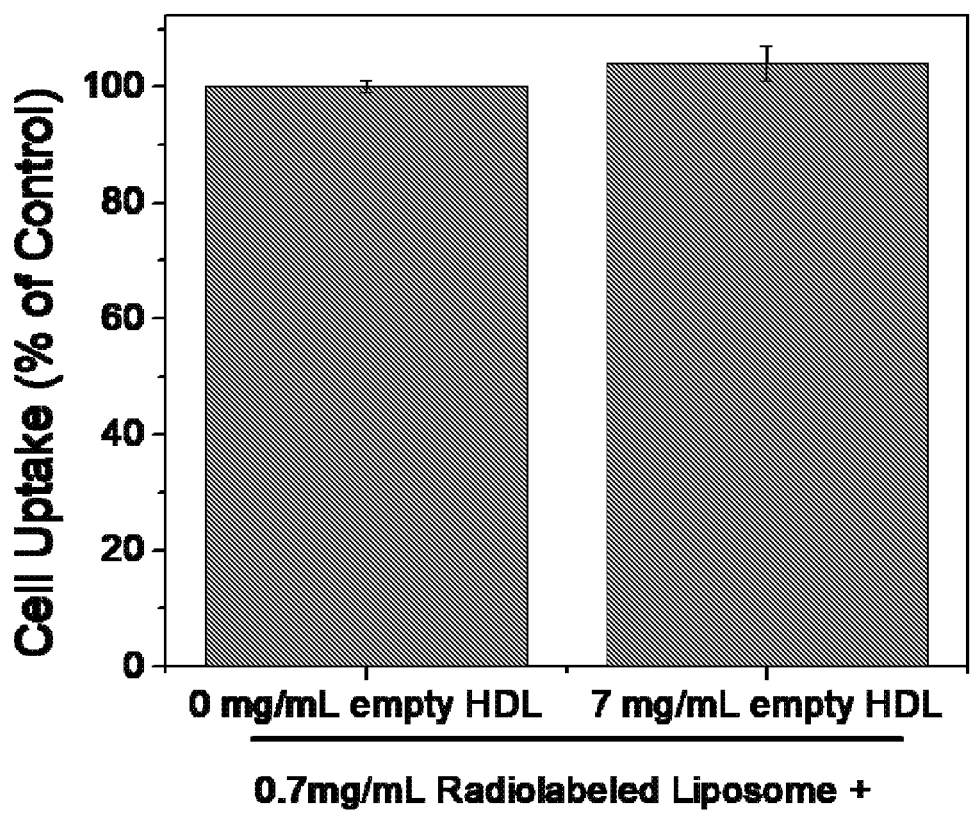
FIG. 7. Radioactivity in cell lysate when radiolabeled liposomes were incubated with and without SR-B1 receptor blocking using empty HDL. No difference in the uptake was observed as liposomes deliver the payload without SR-B1 receptor.

As seen in FIG. 3, the labeled compounds eluted in the same volume and the fraction in both cases (i.e., both labeling liposomes and rHDL). These fractions were visibly cloudy, facilitating their visual detection. In order to assure that the radioactivity in the NP fractions is due to the internalization of the $^{99m}$Tc-complex into the nanoparticles and not due to the co-elution of aggregated or free compound with the NPs, the most radioactive fraction (which was also the cloudiest) was centrifuged using a centrifugation tube containing a dialysis membrane of MWCO of In-Vitro Cell Uptake Study All of the radioactivity uptake by the cell was found in the cytoplasm when the rHDL NPs were used to deliver the radio-imaging agent. Moreover, a partial blocking of SR-B1 receptor with increasing concentrations of empty rHDL as competitive inhibitor, markedly decreased the total uptake of the labeled rHDL by about 60% (the remainder ascribed to membranous accumulation; data not shown). Liposome delivery did not change with HDL blocking as the method of internalization of liposomal radioisotope is independent of SR-B1 expression and hence no change was observed (FIG. 7). The other two groups, $^{99m}$Tc-HYNIC-DA and $^{99m}$TCO$_4^-$, salt were used as controls resulting in only marginal incorporation into cells (data not shown).

Figure 5:
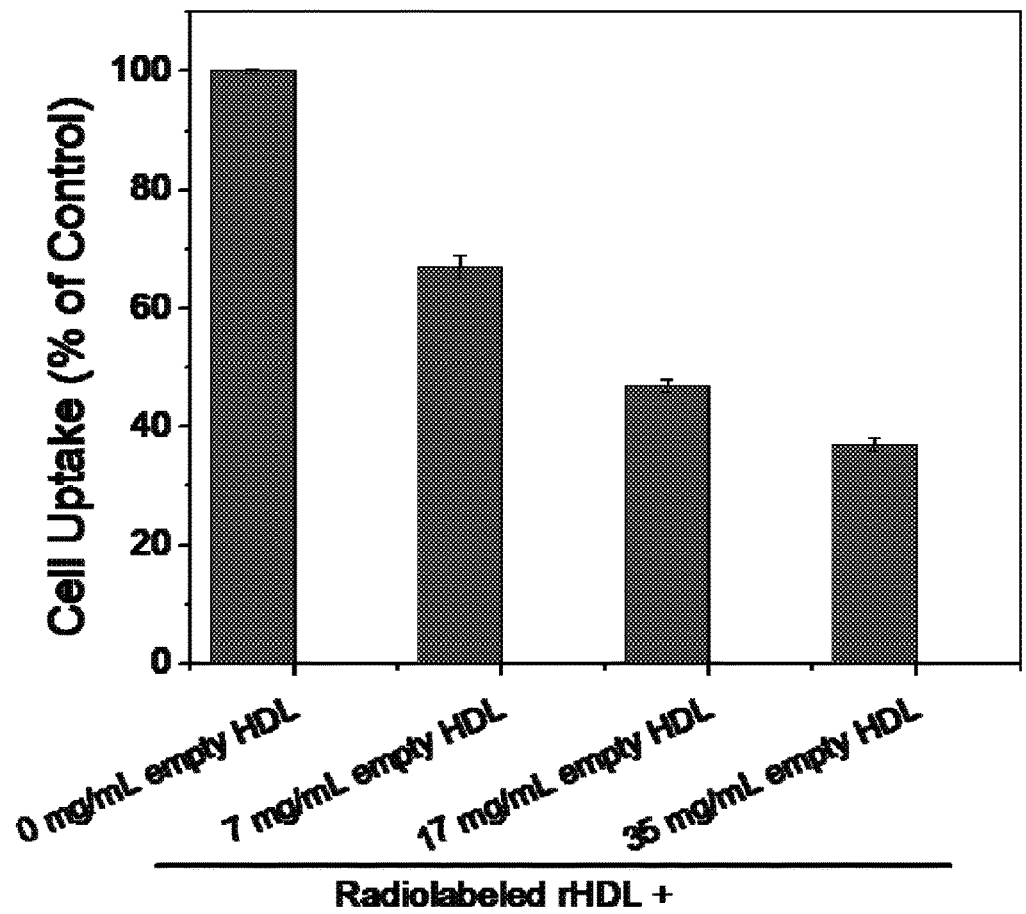
FIG. 5. In vitro cell uptake experiment with and without blocking agent.

FIG. 7 shows no significant difference in the liposome cell uptake in the presence and absence of unlabeled rHDL (SR-B1 blocking agent). The internalization of the liposome into the cell is through an endocytic mechanism which is different from the SR-B1 mediated non-endocytic delivery. The uptake of liposomes by the cell membrane is anticipated to be due mostly to its adsorption on the cell membrane. Liposomal uptake, therefore, is non-specific. A similar approach of using liposome as a negative control of HDL was also employed by Murphy et al. where they demonstrated that HDL inhibited the activity of CD11b while liposomes did not[5]. Results from FIG. 5 agrees with the findings reported by Mooberry et al.[54]. Moreover, several others have reported the specific recognition of HDL by the SR-B1 receptor by labeling HDL with $^3$H or 14C and blocking the receptor using un-labeled rHDL[55-57].

Although $^{99m}$Tc-HYNIC-DA and $^{99m}$ TcO$_4^-$ are not expected to be found in the solution of $^{99m}$Tc-rHDL as separate species, as it was already purified, and $^{99m}$Tc-HYNIC is stable inside the rHDL, their uptake by PC-3 cells was studied as controls. $^{99m}$Tc-HYNIC-DA showed a total uptake of 34% and 31% without and with SR-B1 blocking respectively. On the other hand, $^{99m}$ TcO$_4^-$ was found to have a total uptake of 2.9% and 2.8% with and without SR-B1 blocking, respectively. These results show, as expected that the uptake of these formulations is very low and nonspecific.

$^{99m}$Tc-DA-HYNIC-HDL Biodistribution and Imaging Studies $^{99m}$Tc-HYNIC-DA-rHDL showed better stability than $^{99m}$Tc-BMEDA-HDL, for this reason, the bio-distribution and imaging studies were only carried out with the $^{99m}$Tc-HYNIC-DA-rHDL.

Although $^{99m}$Tc-HYNIC-DA-Liposome also showed good stability, the bio-distribution of these nanoparticles were not performed because liposome bio-distribution has already been studied[58-60] However, this is the first time that HDL type NPs have been labeled with $^{99m}$Tc, therefore study of its bio-distribution in normal mice at different times post-injection were carried out (Table 3).

TABLE 3

Biodistribution of $^{99m}$Tc-rHDL in normal male balb/C mice

| | % (Injected activity)/(g of tissue) Time post-injection | | | |
|---|---|---|---|---|
| Organs | 0.5 h | 2.0 h | 4.0 h | 24 h |
| Blood | 1.55 ± 0.07 | 0.57 ± 0.08 | 0.31 ± 0.08 | 0.19 ± 0.10 |
| Heart | 2.64 ± 2.50 | 0.75 ± 0.30 | 0.47 ± 0.27 | 0.39 ± 0.36 |
| Spleen | 7.91 ± 0.70 | 19.01 ± 10.33 | 9.78 ± 3.43 | 23.82 ± 4.16 |
| Intestine | 1.41 ± 1.31 | 2.72 ± 2.45 | 1.42 ± 1.57 | 0.21 ± 0.12 |
| Pancreas | 2.18 ± 1.60 | 1.98 ± 2.07 | 1.06 ± 0.98 | 0.62 ± 0.51 |
| Kidney | 5.12 ± 3.77 | 2.55 ± 1.27 | 1.49 ± 0.14 | 0.58 ± 0.13 |
| Liver | 36.23 ± 19.45 | 23.55 ± 1.04 | 20.56 ± 7.54 | 20.66 ± 6.26 |
| Lungs | 23.34 ± 10.69 | 9.64 ± 6.49 | 7.71 ± 2.00 | 1.95 ± 1.80 |
| Muscle | 1.53 ± 1.07 | 0.50 ± 0.30 | 0.25 ± 0.06 | 0.31 ± 0.36 |
| Bone | 3.42 ± 2.87 | 1.02 ± 0.84 | 2.21 ± 1.10 | 1.17 ± 0.84 |
| Brain | 0.56 ± 0.53 | 0.29 ± 0.34 | 0.10 ± 0.07 | 0.04 ± 0.02 |

Table 3 confirms the delivery and hepatobiliary excretion pattern of the $^{99m}$Tc-HYNIC-DA-rHDL NPs. In normal animals rHDL NPs were expected to accumulate in liver tissue, due to its high SR-B31 expression. Hence the increased liver uptake observed with post 0.5 hr time points. These data confirm the passive targeting of the SR-B31 receptors showing a higher concentration of the radio-imaging agent in the liver. Other organs such as spleen, lungs, and kidney showed moderate radioactivity while heart and pancreas exhibited very low radioactivity, due to the established absence of SR-B31 receptors. This observation is particularly important in establishing the targeting potential and limiting the off-target bio-distribution of the payload transported by the rHDL NPs.

TABLE 4

Standard uptake values (SUV mean) of PC3 tumor induced in athymic balb/c mice by tail vein inoculation

| Time (hr) | $^{99m}$Tc-rHDL tumor uptake (SUV mean) | $^{99m}$Tc-Liposomes tumor uptake (SUV mean) |
|---|---|---|
| 0.5 | 0.200 ± 0.061 | 0.147 ± 0.048 |
| 2.0 | 0.312 ± 0.056 | 0.198 ± 0.051 |
| 4.0 | 1.513 ± 0.038 | 0.174 ± 0.047 |
| 24.0 | 2.800 ± 0.021 | 0.037 ± 0.023 |

Moreover, a similar study in tumor-bearing mice was conducted to evaluate tumor uptake as a function of time. Table 4 shows the Standard Uptake Values (SUV) for the $^{99m}$Tc-rHDL and $^{99m}$Tc-Liposomes. In case of rHDL the SUV value increased more than 10 fold in 24 hr while these values remained constant for liposomal preparation during the first few hours, and decreasing after 4 hr as evident from the data. SR-B1 expression on PC3 tumor cells thus attracts the rHDL NPs leading to higher accumulation of $^{99m}$Tc.

TABLE 5

Biodistribution of mice bearing PC3 tumor after intra-tumoral and intravenously injection

| | % (Injected activity)/(g of tissue) | | | Tumor/Organ ratio |
|---|---|---|---|---|
| Organ | 5 min, intratumoral injection | 24 h, intra-tumoral injection | 24 h, intravenously injection | 24 h, intravenously injection |
| Blood | 0.11 ± 0.10 | 0.31 ± 0.15 | 0.16 ± 0.09 | 37* |
| Heart | 2.50 ± 0.98 | 0.06 ± 0.07 | 0.60 ± 0.31 | 7.6 |
| Spleen | 0.20 ± 0.14 | 0.73 ± 0.62 | 16.03 ± 5.8 | 0.4 |
| Intestine | 0.24 ± 0.19 | 0.01 ± 0.02 | 0.51 ± 0.36 | 4 |
| Pancreas | 0.21 ± 0.08 | 0.15 ± 0.11 | 2.51 ± 1.1 | 2.7 |
| Kidney | 0.78 ± 0.47 | 0.53 ± 0.25 | 1.29 ± 0.63 | 2.5 |
| Liver | 1.16 ± 0.41 | 1.13 ± 0.61 | 32.14 ± 8.6 | 0.01 |
| Lungs | 6.32 ± 2.1 | 0.01 ± 0.03 | 1.81 ± 1.51 | 3.6 |
| Muscle | 0.28 ± 0.10 | 0.41 ± 0.19 | 1.54 ± 0.39 | 3.87 |
| Bone | 0.14 ± 0.09 | 0.19 ± 0.11 | 1.12 ± 1.01 | 5.7 |
| Tumor | 88.50 ± 3.24 | 30.75 ± 5.32 | 5.96 ± 2.03 | 1 |

*Ratio calculated as % IA/g(Tumor)/% IA/g(Blood)

Table 5 shows the bio-distributions after 5 min and 24 h following intra-tumoral injections, as well as the bio-distributions after 24 h of intravenously injected $^{99m}$Tc-HYNIC-DA-rHDL in mice bearing subcutaneous PC3 tumors. The tumor/organ ratio after 24 h of intravenous injection is also shown. Liver, spleen and tumor showed a significantly higher activity after intravenous injection suggesting efficient targeting to tumor tissue. In fact, tumor tissue radioactivity was substantially higher compared to heart, blood, intestine, pancreas, kidney, lungs, muscles, and bones. This is especially important for the delivery of chemotherapy drugs such as doxorubicin where cardiotoxicity is a major concern. In case of the heart, the amount received was ten fold less compared to tumor tissue at 24 hrs.

Figure 6B:
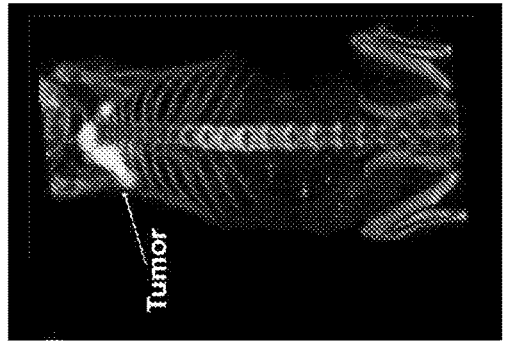
FIGS. 6A-6D. SPECT/CT images after 4 h of post injection of $^{99m}$Tc-rHDL in athymic mice bearing PC3 tumor induced subcutaneously, (A) intravenous injection and (B) intra-tumoral injection. SPECT/CT images after 4 h of post injection intravenously in athymic mice bearing PC3 tumor induced by tail vein inoculation, (C) $^{99m}$Tc-rHDL and (D)$^{99m}$Tc-Liposomes.
Figure 6D:
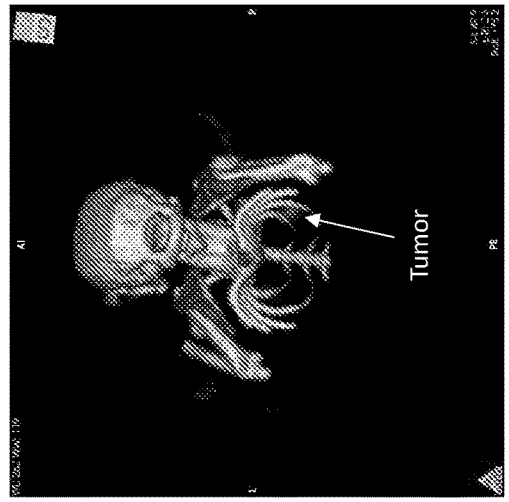
Figure 6A:
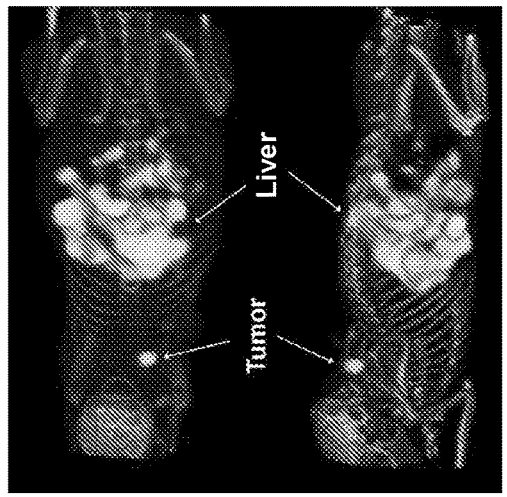
Figure 6C:
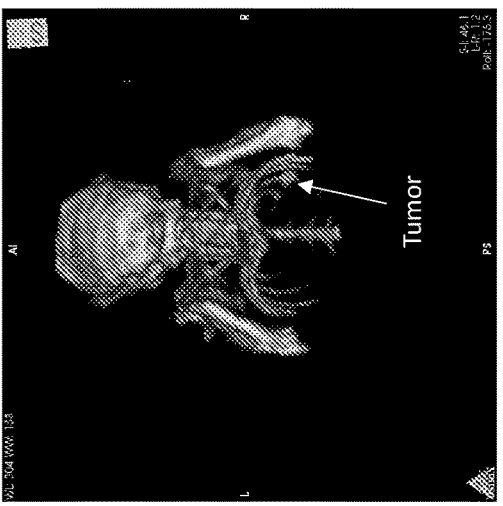
Figure 8:
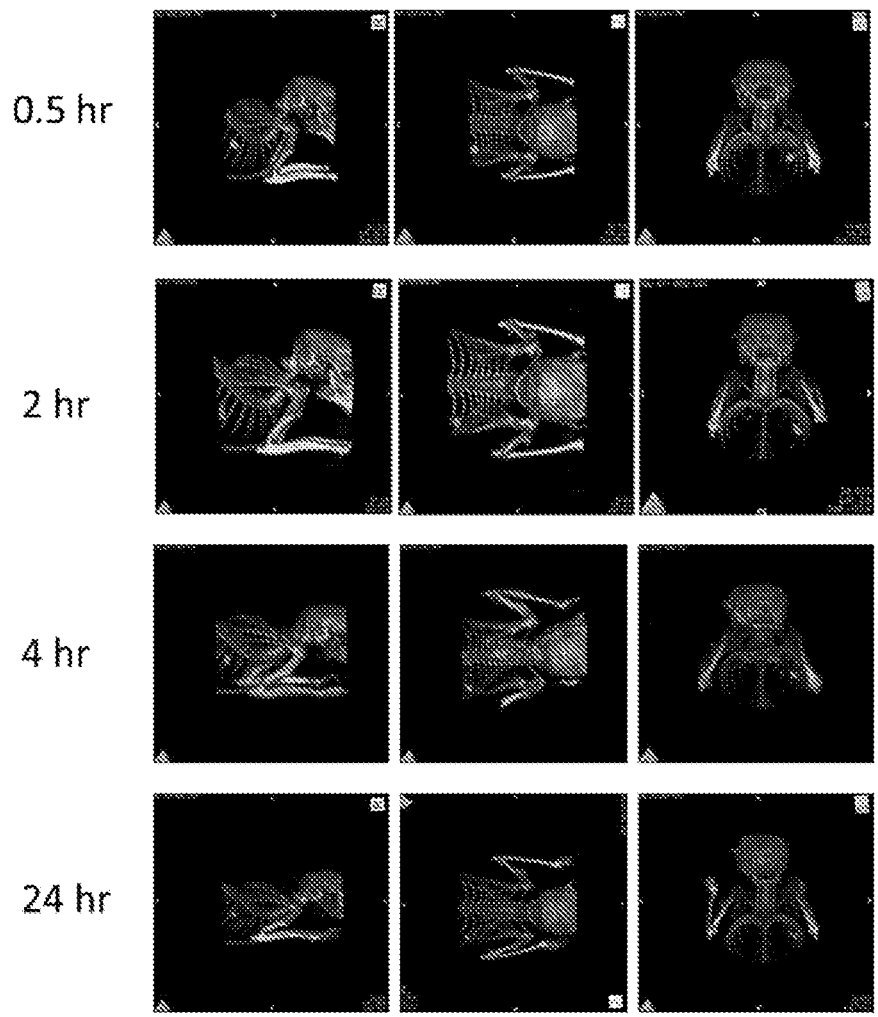
FIG. 8. SPECT/CT images at different time-points post $^{99m}$Tc-rHDL injection intravenously in athymic mice bearing PC3 tumor induced by tail vein inoculation.

FIGS. 6A and 6B show the SPECT/CT images after four hours following intravenous (FIG. 6A) and intra-tumoral injection (FIG. 6B), respectively on mice bearing a PC3 tumor. As expected, radioactivity is accumulated in the PC3 tumor, due to the overexpression of SR-B1 receptors that mediate the internalization of the rHDL payload ($^{99m}$Tc-HYNIC-DA). The high accumulation of $^{99m}$Tc-rHDL in the liver is consistent with the bio-distribution results shown in Table 5. FIGS. 6C and 6D show the SPECT/CT images after 4 hr of intravenous injection in mice bearing a PC3 tumor induced by tail-vein inoculation. It was expected that PC3 cancer cells tend to harbor in the lungs predominantly. Thus, we see a higher uptake in these cells in lung tissue where PC3 cells are lodged. Images correlate with the SUV mean values reported in Table 4 and also highlight the receptor-specific uptake of rHDL nanoparticles. Additional time-course images of radiolabeled rHDL are shown in FIG. 8.

$^{99m}$Tc-HYNIC-DA-rHDL Radiokinetic Model

Table 6 shows the radiocokinetic model and the total disintegrations occurred in the excretory organs and tumor after the administration of $^{99m}$Tc-HYNIC-DA-rHDL. The long residence time of total disintegrations of $^{99m}$Tc-rHDL in the tumor, which is 15 times higher than the $^{99m}$Tc-liposomes, is noteworthy. Although we are aware of the preferable non-endocytic delivery of payloads from the rHDL NPs, we are not certain regarding the exact delivery mechanism that facilitated the enhanced tumor accumulation and retention of $^{99m}$Tc.

These types of studies are beyond the scope of the current investigation. Perhaps, these findings may be ascribed to efficient targeting via SR-B1 and the lack of well-developed venous structure in the tumor mass that may facilitate the extended retention of $^{99m}$Tc-DA at the tumor site. The substantially extended retention time of $^{99m}$Tc-rHDL justifies its use in tumor imaging, and also suggest an effective therapeutic application for the rHDL platform; therefore, these NPs could be most useful for the development of theranostic radio-nano-pharmaceuticals.

TABLE 6

Radiokinetic model for excretory organs and tumors

| Organ | Radiokinetic model | Total disintegrations (MBq h/MBq) $\int_{t=0}^{t=\infty} Ah(t)dt$ |
|---|---|---|
| Liver | $A(t) = -90e^{-(12.72)t} + 29.1e^{-(1.23)t} + 21.5e^{-(0.115)t}$ | 2.030 |
| Spleen | $A(t) = -2.0e^{-(0.91)t} + 388e^{-(10.115)t} + 2.11e^{-(0.115)t}$ | 0.199 |
| Kidney | $A(t) = -1.59e^{-(207.115)t} - 1.29e^{-(17.315)t} + 1.63e^{-(0.511)t}$ | 0.031 |

TABLE 6-continued

Radiokinetic model for excretory organs and tumors

| Organ | Radiokinetic model | Total disintegrations (MBq h/MBq) $\int_{t=0}^{t=\infty} Ah(t)dt$ |
|---|---|---|
| Tumor | $A(t) = -3.08e^{-(0.281)t} - 0.266e^{-(33.115)t} + 2.87e^{-(0.115)t}$ | 0.139 |
| Tumor-$^{99m}$Tc-Liposome | $A(t) = -2.32e^{-(0.438)t} - 0.158e^{-(3.195)t} + 2.48e^{-(0.395)t}$ | 0.009 |

CONCLUSIONS

6-Hydrazinopyridine-3-carboxylic acid dodecylamide (HYNIC-DA) was synthesized and labeled with $^{99m}$Tc nuclide, achieving high radiochemical purity. The $^{99m}$Tc-complex is more hydrophobic than conventional $^{99m}$Tc-BMEDA, perhaps resulting in 90% of $^{99m}$Tc-HYNIC-DA remaining entrapped into liposomes and rHDL after three hours of incubation. Therefore, $^{99m}$Tc-HYNIC-DA is a good alternative to label amphiphilic nanoparticles such as rHDL and liposomes with adequate efficiency and stability. Biodistribution and imaging studies carried out with PC3 tumors carrying mice showed high radioactivity uptake in the tumor and the liver apparently due to the SR-B1 targeting and subsequent payload accumulation. Findings from in vivo studies are consistent with those from in vitro cell uptake studies where the specific recognition of $^{99m}$Tc-rHDL was demonstrated by SR-B1 blockade with unlabeled rHDL and control experiment with $^{99m}$Tc-Liposome evaluated the nonspecific uptake. Determination of SUVs also agree with cell uptake experiments, showing higher values with $^{99m}$Tc-rHDL compared to $^{99m}$Tc-Liposomes (steady and lower SVU mean values). This nanosystem ($^{99m}$Tc-rHDL) shows favorable properties that warrant consideration as a radiopharmaceutical for the diagnosis of cancers, especially those exhibiting overexpressed SR-B1 receptors. Combining the drug delivery capabilities of rHDL as well as its potential as a radiopharmaceutical transporter for diagnosis, rHDL NPs may also be utilized in the design of a broad range of new theranostic radiopharmaceuticals.

REFERENCES

1 Z. Cheng, A. Al Zaki, J. Z. Hui, V. R. Muzykantov and A. Tsourkas, *Science*, 2012, 338, 903-910, DOI: 10.1126/science.1226338 [doi].
2 G. Bao, S. Mitragotri and S. Tong, *Annu. Rev. Biomed. Eng.*, 2013, 15, 253-282.
3 J. V. Jokerst and S. S. Gambhir, *Acc. Chem. Res.*, 2011, 44, 1050-1060.
4 P. Debbage and W. Jaschke, *Histochem. Cell Biol.*, 2008 130, 845-875.
5 T. O. Munnink, W. Nagengast, A. Brouwers, C. Schroder, G. Hospers, M. Lub-de Hooge, E. Van der Wall, P. Van Diest and E. De Vries, *The Breast*, 2009, 18, S66-S73.
6 H. Hricak, P. L. Choyke, S. C. Eberhardt, S. A. Leibel and P. T. Scardino, *Radiology*, 2007, 243, 28-53.
7 W. J. Mulder, G. J. Strijkers, G. A. van Tilborg, A. W. Griffioen and K. Nicolay, *NMR Biomed.*, 2006, 19, 142-164.
8 A. M. Lees, R. S. Lees, F. J. Schoen, J. L. Isaacsohn, A. J. Fischman, K. A. McKusick and H. W. Strauss, *Arteriosclerosis*, 1988, 8, 461-470.
9 J. C. Frias, M. J. Lipinski, S. E. Lipinski and M. T. Albelda, *Contrast media & molecular imaging*, 2007, 2, 16-23.
10 M. Mangaraj, R. Nanda and S. Panda, *Indian Journal of Clinical Biochemistry*, 2016, 31, 253-259.
11 J. B. Simonsen, Nanomedicine: Nanotechnology, Biology and Medicine, 2016, 12, 2161-2179.
12 A. G. Lacko, M. Nair, S. Paranjape, L. Mooberry and W. J. McConathy, *Chemotherapy*, 2006, 52, 171-173, DOI: 93268 [pii].
13 A. G. Lacko, N. A. Sabnis, B. Nagarajan and W. J. McConathy, *Front. Pharmacol.*, 2015, 6, 247, DOI: 10.3389/fphar.2015.00247 [doi].
14 Q. Lin, J. Chen, K. K. Ng, W. Cao, Z. Zhang and G. Zheng, *Pharm. Res.*, 2014, 31, 1438-1449.
15 S. Acton, A. Rigotti, K. T. Landschulz, S. Xu, H. H. Hobbs and M. Krieger, *Science*, 1996, 271(5248), 518-520.
16 R. Kuai, D. Li, Y. E. Chen, J. J. Moon and A. Schwendeman, *ACS nano*, 2016, 10(3), 3015-3041.
17 N. Sabnis, S. Pratap, P. Bowman, I. Akopova and A. G. Lacko, *Frontiers in pediatrics*, 2013, 1, 6.
18 N. Sabnis, M. Nair, M. Israel, W. J. McConathy and A. G. Lacko, *Int. J. Nanomedicine*, 2012, 7, 975-983, DOI: 10.2147/IJN.S28029 [doi].
19 S. Yang, M. G. Damiano, H. Zhang, S. Tripathy, A. J. Luthi, J. S. Rink, A. V. Ugolkov, A. T. Singh, S. S. Dave, L. I. Gordon and C. S. Thaxton, *Proc. Natl. Acad. Sci. U.S.A*, 2013, 110, 2511-2516. DOI: 10.1073/pnas.1213657110 [doi].
20 P. M. Cruz, H. Mo, W. J. McConathy, N. Sabnis and A. G. Lacko, Front. *Pharmacol.*, 2013, 4, 119. DOI: 10.3389/fphar.2013.00119 [doi].
21 A. Fiorenza, A. Branchi and D. Sommariva, *Int. J. Clin. Lab. Res.*, 2000, 30, 141-145.
22 J. L. Gutierrez-Pajares, C. B. Hassen, S. Chevalier and P. G. Frank, *Frontiers in pharmacology*, 2016, 7, 338.
23 E. Kökoğlu, I. Karaarslan, H. M. Karaarslan and H. Baloğlu, *Cancer Lett.*, 1994, 82, 175-178.
24 V. Michalaki, G. Koutroulis, K. Syrigos, C. Piperi and A. Kalofoutis, *Mol. Cell. Biochem.*, 2005, 268, 19-24.
25 F. D. Shah, S. N. Shukla, P. M. Shah, H. R. Patel and P. S. Patel, *Integrative cancer therapies*, 2008, 7, 33-41.
26 P. M. Cruz, H. Mo, W. McConathy, N. A. Sabnis and A. G. Lacko, *Frontiers in pharmacology*, 2013, 4, 119.
27 M. M. Shahzad, L. S. Mangala, H. D. Han, C. Lu, J. Bottsford-Miller, M. Nishimura, E. M. Mora, J. Lee, R. L. Stone and C. V. Pecot, *Neoplasia*, 2011, 13, 309IN3-319IN8.
28 Z. Zhang, J. Chen, L. Ding, H. Jin, J. F. Lovell, I. R. Corbin, W. Cao, P. Lo, M. Yang and M. Tsao, *Small*, 2010, 6, 430-437.
29 P. Khumsupan, R. Ramirez, D. Khumsupan and V. Narayanaswami, *Biochimica et BiophysicaActa (BBA)-Biomembranes*, 2011, 1808, 352-359.
30 L. Cui, Q. Lin, W. Jiang, L. Ding, J. Chen and G. Zheng, 2014, BT3A. 55.

31 D. P. Cormode, T. Skajaa, M. M. van Schooneveld, R. Koole, P. Jarzyna, M. E. Lobatto, C. Calcagno, A. Barazza, R. E. Gordon and P. Zanzonico, *Nano letters*, 2008, 8, 3715-3723.

32 C. Perez-Medina, T. Binderup, M. Lobatto, S. Baxter, C. Calcagno, S. Ishino, T. Reiner, J. Lewis, Z. Fayad and W. Mulder, *Journal of Nuclear Medicine*, 2016, 57, 63-63.

33 C. Perez-Medina, J. Tang, D. Abdel-Atti, B. Hogstad, M. Merad, E. A. Fisher, Z. A. Fayad, J. S. Lewis, W. J. Mulder and T. Reiner, *J. Nucl. Med.*, 2015, 56, 1272-1277. DOI: 10.2967/jnumed.115.158956 [doi].

34 H. Sinzinger, H. Bergmann, J. Kaliman and P. Angelberger, *European Journal of Nuclear Medicine and Molecular Imaging*, 1986, 12, 291-292.

35 S. Ishino, T. Mukai, Y. Kuge, N. Kume, M. Ogawa, N. Takai, J. Kamihashi, M. Shiomi, M. Minami, T. Kita and H. Saji, *J. Nucl. Med.*, 2008, 49, 1677-1685. DOI: 10.2967/jnumed.107.049536 [doi].

36 D. P. Cormode, J. C. Frias, Y. Ma, W. Chen, T. Skajaa, K. Briley-Saebo, A. Barazza, K. J. Williams, W. J. Mulder and Z. A. Fayad, *Clinical lipidology*, 2009, 4, 493-500.

37 E. Lim, T. Kim, S. Paik, S. Haam, Y. Huh and K. Lee, *Chem. Rev.*, 2014, 77, 7826-7831.

38 H. Huang and J. F. Lovell, *Advanced functional materials*, 2017, 50, 533-537.

39 A. Fernandez-Fernandez, R. Manchanda and A. J. McGoron, *Appl. Biochem. Biotechnol.*, 2011, 165(7-8), 1628-1651.

40 C. N. McEwen, R. G. McKay and B. S. Larsen, *Anal. Chem.*, 2005, 77, 7826-7831.

41 S. Szarka and L. Prokai, *Journal of Mass Spectrometry*, 2015, 50, 533-537.

42 A. Toro-Córdova, F. Ledezma-Gallegos, L. Mondragon-Fuentes, R. Jurado, L. A. Medina, J. M. Pérez-Rojas and P. Garcia-Lopez, *J. Chromatogr. Sci.*, 2016, 54, 1016-1021.

43 F. Szoka Jr and D. Papahadjopoulos, *Proc. Natl. Acad. Sci. U.S.A*, 1978, 75, 4194-4198.

44 J. C. M. Stewart, *Anal. Biochem.*, 1980, 104, 10-14.

45 C. L. Santos-Cuevas, G. Ferro-Flores, C. A. de Murphy, F. d. M. Ramírez, M. A. Luna-Gutiérrez, M. Pedraza-López, R. Garcia-Becerra and D. Ordaz-Rosado, *Int. J. Pharm.*, 2009 375, 75-83.

46 G. Ferro-Flores, C. Arteaga de Murphy, J. Rodriguez-Cortes, M. Pedraza-Lopez and M. T. Ramirez-Iglesias, *Nucl. Med. Commun.*, 2006, 251, 7-13. DOI: 10.1097/01.mnm.0000202863.52046.7f [doi].

47 B. E. Ocampo-García, F. d. M. Ramirez, G. Ferro-Flores, L. M. De León-Rodriguez, C. L. Santos-Cuevas, E. Morales-Avila, C. A. de Murphy, M. Pedraza-López, L. A. Medina and M. A. Camacho-López, *Nucl. Med. Biol.*, 2011, 38, 1-11.

48 E. Morales-Avila, G. Ferro-Flores, B. E. Ocampo-Garcia, L. M. De León-Rodriguez, C. L. Santos-Cuevas, R. Garcia-Becerra, L. A. Medina and L. Gómez-Oliván, *Bioconjug. Chem.*, 2011, 22, 913-922.

49 Technical Report Series No 466, in ed. International Atomic Energy Agency, Vienna, 2008, p. 7-26.

50 A. Bao, B. Goins, R. Klipper, G. Negrete, M. Mahindaratne and W. T. Phillips, *J. Pharm. Sci.*, 2003, 92, 1893-1904.

51 C. L. Santos-Cuevas, G. Ferro-Flores, C. A. de Murphy and P. A. Pichardo-Romero, *Nucl. Med. Commun.*, 2008, 29, 741-747.

52 G. Ferro-Flores, F. Ramirez, M. Martinez-Mendoza, C. Murphy, M. Pedraza-Lopez and L. Garcia-Salinas, *J. Radioanal. Nucl.*, 2002, 251, 7-13.

53 A. J. Murphy, K. J. Woollard, A. Hoang, N. Mukhamedova, R. A. Stirzaker, S. P. McCormick, A. T. Remaley, D. Sviridov and J. Chin-Dusting, *Arterioscler. Thromb. Vasc. Biol.*, 2008, 28(11), 2071-2077.

54 L. K. Mooberry, M. Nair, S. Paranjape, W. J. McConathy and A. G. Lacko, *J. Drug Target.*, 2010, 18(1), 53-58.

55 T. A. Pagler, S. Rhode, A. Neuhofer, H. Laggner, W. Strobl, C. Hinterndorfer, I. Volf, M. Pavelka, E. R. Eckhardt, D. R. van der Westhuyzen, G. J. Schutz and H. Stangl, *J. Biol. Chem.*, 2006, 281(16), 11193-11204. DOI: M510261200 [pii].

56 M. A. Connelly, *Mol. Cell. Endocrinol.*, 2009, 300(1-2), 83-88. DOI: 10.1016/j.mce.2008.09.011 [doi].

57 M. C. de Beer, L. W. Castellani, L. Cai, A. J. Stromberg, F. C. de Beer and D. R. van der Westhuyzen, *J. Lipid Res.*, 2004, 45(4), 706-715. DOI: 10.1194/jlr.M300417-JLR200 [doi].

58 E. T. M. Dams, W. J. Oyen, O. C. Boerman and G. Storm, *The Journal of Nuclear Medicine*, 1998, 39, 2172.

59 P. Laverman, O. C. Boerman and G. Storm, *Meth. Enzymol.*, 2003, 373, 234-248.

60 de Barros, André Luis Branco, L. das Graças Mota, D. C. F. Soares, M. M. A. Coelho, M. C. Oliveira and V. N. Cardoso, *Bioorg. Med. Chem. Lett.*, 2011, 21, 7373-7375.

We claim:

1. Reconstituted high-density lipoprotein (rHDL) nanoparticles (rHDL NPs) comprising hydrazinonicotinic acid (HYNIC)-N-dodecylamide.

2. The rHDL NPs according to claim 1, wherein said hydrazinonicotinic acid (HYNIC)-N-dodecylamide is labeled with a rhenium (Re) or technetium (Tc) radioisotope.

3. A composition comprising a pharmaceutically acceptable carrier and an rHDL nanoparticle according to claim 1.

4. A method of treating cancer in a subject comprising administering a rHDL nanoparticle according to claim 2 or a composition comprising said rHDL nanoparticle and a pharmaceutically acceptable carrier to a subject having a cancer.

5. The method according to claim 4, wherein said cancer expresses scavenger receptor type B1 (SR-B1).

6. The method according to claim 4, wherein said cancer is selected from breast cancer, colon cancer, ovarian cancer, prostate cancer, liver cancer, epithelial cancer, melanoma and lymphoma.

7. The method according to claim 4, wherein said method comprises treating a subject having cancer subject to whom radiolabeled rHDL are administered, said radiolabeled rHDL being labeled with a Tc or Re radioisotope that emits beta radiation.

8. A method of synthesizing hydrazinonicotinic acid (HYNIC)-N-dodecylamide comprising reacting 6-chloropyridine-3-carboxylic acid with dodecylamine to form an amide and reacting said amide with hydrazine to form 6-hydrazinopyridine-3-carboxylic acid dodecylamide (HYNIC-DA).

9. The method according to claim 8, said method comprising contacting dodecylamine, 6-chloropyridine-3-carboxylic acid, 1-hydroxybenzotriazole and N,N'-diisopropylcarbodiimide.

10. The method according to claim 9, wherein said 1-hydroxybenzotriazole is anhydrous.

11. The method according to claim 8, said method further comprising isolation of 6-chloropyridine-3-carboxylic acid dodecylamide.

12. The method according to claim 8, said method further comprising contacting said 6-chloropyridine-3-carboxylic acid dodecylamide with hydrazine to form hydrazinonicotinic acid (HYNIC)-N-dodecylamide.

13. The method according to claim 12, said method further comprising isolation of hydrazinonicotinic acid (HYNIC)-N-dodecylamide.

14. The method according to claim 8, said method further comprising contacting ethylenediamine-N, N'-diacetic acid (EDDA)-tricine solution SnCl$_2$ and $^{99m}$Tc-pertechnetate with HYNIC-DA to form $^{99m}$Tc radiolabeled HYNIC-DA.

15. The method according to claim 8, said method further comprising contacting said HYNIC-DA with rHDL to form rHDL comprising said HYNIC-DA, said HYNIC-DA being radiolabeled or not radiolabeled.

16. The method according to claim 15, wherein HYNIC-DA is not radiolabeled.

17. The method according to claim 15, wherein HYNIC-DA is radiolabeled.

18. The method according to claim 17, wherein HYNIC-DA is radiolabeled with a Tc or Re radioisotope.

19. The rHDL NPs according to claim 2, wherein said hydrazinonicotinic acid (HYNIC)-N-dodecylamide is labeled with $^{92}$Tc, $^{93c}$Tc, $^{93g}$Tc, $^{93m}$Tc, $^{94g}$Tc, $^{94m}$Tc, $^{95g}$Tc, $^{95m}$Tc, $^{96g}$Tc, $^{96m}$Tc, $^{97m}$Tc, $^{99m}$Tc, $^{178}$Re, $^{180}$Re, $^{180}$Re, $^{180}$Re, $^{181}$Re, $^{182}$Re, $^{183}$Re, $^{184}$Re, $^{184}$Re, $^{186}$Re, $^{188m}$Re, $^{188}$Re, $^{189}$Re or $^{190}$Re.

20. The method according to claim 18, wherein HYNIC-DA is radiolabeled with $^{92}$Tc, $^{93c}$Tc, $^{93g}$Tc, $^{93m}$Tc, $^{94g}$Tc, $^{94m}$Tc, $^{95g}$Tc, $^{95m}$Tc, $^{96g}$Tc, $^{96m}$Tc, $^{97m}$Tc, $^{99m}$Tc, $^{178}$Re, $^{180}$Re, $^{180}$Re, $^{180}$Re, $^{181}$Re, $^{182}$Re, $^{183}$Re, $^{184}$Re, $^{184}$Re, $^{186}$Re, $^{188m}$Re, $^{188}$Re, $^{189}$Re or $^{190}$Re.

21. A method of imaging cancer in a subject comprising administering a rHDL nanoparticle according to claim 2 or a composition comprising said rHDL nanoparticle and a pharmaceutically acceptable carrier to a subject having a cancer and imaging the subject.

22. The method according to claim 21, wherein said method comprises imaging a subject to whom radiolabeled rHDL are administered, said imaging being performed by single photon emission computed tomography (SPECT) and/or X-ray computed tomography (CT) and said radiolabeled rHDL being labeled with a Tc or Re radioisotope that emits gamma radiation.

23. The method according to claim 21, wherein said cancer is selected from breast cancer, colon cancer, ovarian cancer, prostate cancer, liver cancer, epithelial cancer, melanoma and lymphoma.

* * * * *